US012734345B2

(12) United States Patent
Prasad et al.

(10) Patent No.: US 12,734,345 B2
(45) Date of Patent: Sep. 15, 2026

(54) SKIN DISINFECTANT WIPE

(71) Applicant: Becton, Dickinson and Company, Franklin Lakes, NJ (US)

(72) Inventors: Shishir Prasad, Ramsey, NJ (US); Kevin M. Ryan, Whitehouse Station, NJ (US); Rahul Malviya, Salmon Arm (CA); Shashwat Jain, Indore (IN); Vineeth Acharya, Udupi (IN); Ravi Kaushik, Delhi (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 278 days.

(21) Appl. No.: 18/684,213

(22) PCT Filed: Aug. 16, 2022

(86) PCT No.: PCT/US2022/040469
§ 371 (c)(1),
(2) Date: Feb. 16, 2024

(87) PCT Pub. No.: WO2023/023061
PCT Pub. Date: Feb. 23, 2023

(65) Prior Publication Data
US 2024/0350781 A1 Oct. 24, 2024

Related U.S. Application Data

(60) Provisional application No. 63/234,110, filed on Aug. 17, 2021.

(51) Int. Cl.
*A45D 34/04* (2006.01)
*A45D 37/00* (2006.01)
*A61M 35/00* (2006.01)

(52) U.S. Cl.
CPC .......... *A61M 35/006* (2013.01); *A45D 34/04* (2013.01); *A45D 37/00* (2013.01)

(58) Field of Classification Search
CPC ...... A61M 35/006; A45D 34/04; A45D 37/00
See application file for complete search history.

(56) References Cited

U.S. PATENT DOCUMENTS 3,466,131 A * 9/1969 Arcudi .................. B65D 83/00 401/196
3,485,562 A * 12/1969 Cairns .................. B05C 17/002 401/196

(Continued)

FOREIGN PATENT DOCUMENTS

EP 0272492 A2 6/1988
EP 2499914 A1 * 9/2012 ............. A61P 31/00

(Continued)

*Primary Examiner* — Guy K Townsend
(74) *Attorney, Agent, or Firm* — The Webb Law Firm

(57) ABSTRACT

A skin preparation device for applying an antiseptic composition to skin of a patient that includes an applicator configured to absorb the antiseptic composition, the applicator comprising a top surface and a bottom surface, the bottom surface configured to apply the antiseptic composition to the skin of the patient, and a gripping portion configured to provide a portion of the skin preparation device that is gripped by a user when using the skin preparation device.

13 Claims, 16 Drawing Sheets

(56) References Cited

U.S. PATENT DOCUMENTS

| | | | | | |
|---|---|---|---|---|---|
| 3,826,259 | A * | 7/1974 | Bailey | A61M 35/006 604/3 |
| 4,183,684 | A * | 1/1980 | Avery, Jr. | A45D 34/04 401/133 |
| 5,368,581 | A * | 11/1994 | Smith | A61M 35/006 604/289 |
| 5,690,958 | A | 11/1997 | McGrath | |
| 5,775,826 | A * | 7/1998 | Miller | A45D 34/04 401/133 |
| 6,516,947 | B1 * | 2/2003 | Van Dyke | A61M 35/006 604/363 |
| 6,533,484 | B1 * | 3/2003 | Osei | A61M 35/006 401/133 |
| 6,916,133 | B2 * | 7/2005 | Hoang | A61M 35/006 401/133 |
| 8,491,212 | B2 * | 7/2013 | Castel | A61F 13/38 401/133 |
| D718,131 | S * | 11/2014 | Brown | D9/447 |
| 9,220,881 | B2 * | 12/2015 | Kaufman | A61L 2/18 |
| 9,775,977 | B2 * | 10/2017 | Dombrowski | A61M 35/006 |
| 2004/0068218 | A1 * | 4/2004 | Davis | A61M 35/006 401/196 |
| 2004/0253039 | A1 * | 12/2004 | Stenton | A61M 35/003 401/132 |
| 2004/0267182 | A1 * | 12/2004 | Davis | A61L 2/18 604/2 |
| 2010/0168637 | A1 * | 7/2010 | Casey | B65D 83/771 401/133 |
| 2010/0168638 | A1 * | 7/2010 | Korogi | A61M 35/006 401/133 |
| 2010/0226706 | A1 * | 9/2010 | Flores | A61M 35/006 401/133 |
| 2010/0257685 | A1 * | 10/2010 | Tuman | C11D 17/049 15/244.4 |
| 2011/0066121 | A1 * | 3/2011 | Hoang | A61M 35/006 29/428 |
| 2012/0237452 | A1 * | 9/2012 | Colomer | A61P 31/00 424/10.3 |
| 2014/0126949 | A1 * | 5/2014 | Kaufman | A61M 35/006 401/132 |
| 2014/0371695 | A1 * | 12/2014 | Chiang | A61M 35/006 604/310 |
| 2016/0106964 | A1 * | 4/2016 | Quaglia | A61M 35/006 604/310 |
| 2018/0071503 | A1 * | 3/2018 | Brown | A61M 35/006 |
| 2018/0126137 | A1 * | 5/2018 | Kaufman | A61M 35/003 |
| 2022/0346524 | A1 * | 11/2022 | Blagg | A45D 34/04 |
| 2023/0166091 | A1 * | 6/2023 | Huenerfauth | A61B 90/80 604/290 |
| 2024/0350781 | A1 * | 10/2024 | Prasad | A61M 35/006 |

FOREIGN PATENT DOCUMENTS

| | | | |
|---|---|---|---|
| EP | 2499914 | B1 | 12/2017 |
| WO | 2013162882 | A1 | 10/2013 |
| WO | 2023196179 | A1 | 10/2023 |

* cited by examiner

SKIN DISINFECTANT WIPE

CROSS-REFERENCE TO RELATED APPLICATIONS

This application is the United States national phase of International Application No. PCT/US2022/040469 filed Aug. 16, 2022, and claims priority to U.S. Provisional Application Ser. No. 63/234,110, filed Aug. 17, 2021, entitled "Skin Disinfectant Wipe", the entire disclosures of which are hereby incorporated by reference in their entireties.

BACKGROUND OF THE INVENTION

Field of the Invention

The present disclosure is directed to a skin disinfectant wipe and, more particularly, is directed to a skin disinfectant wipe that reduces or eliminates contact between a user's skin surface and a patient's skin surface when applying the disinfectant to the patient's skin surface.

Description of Related Art

Proper cleansing and disinfecting a patient's skin, for example but not limited to, preparing for injection or aspiration through the patient's skin, or a surgery site is crucial to reduce the likelihood of adverse events, including infection, during and following the intervention. However, for many reasons ranging from pressure to rapidly prepare a patient for these procedures to distractions inherent in the environment, many clinicians and other staff do not engage in proper cleansing and disinfecting techniques, for example such as the suggested guidelines of 30 seconds of cleansing, followed by 30 seconds of drying for dry skin areas.

Further, a current method for patient skin preparation is dominated by the use of disinfectant wipes. These disinfectant wipes tend to lead to accidental touching of the patient's skin by the user applying the disinfectant wipe and improper aseptic technique, which both lead to contamination and increased rate of infection on the patient's skin surface.

SUMMARY OF THE INVENTION

In view of the foregoing disclosure, there is a current need in the art for a disinfectant wipe that reduces or eliminates contact between a user's skin surface and a patient's skin surface when applying the disinfectant to the patient's skin surface. A further need exists in the art for a disinfectant wipe that reduces or eliminates contact between a user's skin surface and a patient's skin surface when applying the disinfectant to the patient's skin surface and remains cost-effective for mass production.

In some non-limiting embodiments and aspects of the present disclosure, a skin preparation device for applying an antiseptic composition to skin of a patient may include an applicator configured to absorb the antiseptic composition, the applicator comprising a top surface and a bottom surface, the bottom surface configured to apply the antiseptic composition to the skin of the patient, and a gripping portion configured to provide a portion of the skin preparation device that is gripped by a user when using the skin preparation device.

In some non-limiting embodiments or aspects of the present disclosure, the applicator and the gripping portion may be made of the same material. The gripping portion may be a ring-shaped structure. The gripping portion may be formed from opposing ends of the skin preparation device that are bent away from the applicator. The applicator and gripping portion may be formed from a single piece of material.

In one non-limiting embodiment or aspect, a skin preparation device for applying an antiseptic composition to skin of a patient may include an applicator configured to absorb the antiseptic composition, the applicator comprising a top surface and a bottom surface, the bottom surface configured to apply the antiseptic composition to the skin of the patient, and a holding portion that receives the applicator to provide a portion of the skin preparation device that is gripped by a user when using the skin preparation device.

In some non-limiting embodiments or aspects, the applicator and the holding portion may be made of a different material. The applicator may be made of a sponge material and the holding portion is made of a plastic material. The holding portion may include at least one reinforcing member to provide support to the applicator. The holding portion may define a cavity that receives at least a portion of the applicator.

In one configuration, a skin preparation device for applying an antiseptic composition to skin of a patient includes an applicator configured to absorb the antiseptic composition, the applicator including a top surface and a bottom surface, the bottom surface configured to apply the antiseptic composition to the skin of the patient, and a holding portion that receives the applicator to provide a portion of the skin preparation device that is gripped by a user when using the skin preparation device.

In certain configurations, the applicator and the holding portion are made of a different material.

In certain configurations, the applicator is made of a sponge material and the holding portion is made of a plastic material.

In certain configurations, the holding portion includes at least one reinforcing member to provide support to the applicator.

In certain configurations, the holding portion defines a cavity that receives at least a portion of the applicator.

In certain configurations, the applicator is at least one of a natural sponge and a synthetic sponge.

In certain configurations, the synthetic sponge includes at least one of a polyurethane, a polyester, and/or a vegetal cellulose.

In certain configurations, the antiseptic composition includes one or more alcohols, comprising ethyl alcohol, propyl alcohol, isopropyl alcohol, n-propanol, and/or mixtures thereof.

In certain configurations, the antiseptic composition includes one or more non-alcohol based compounds.

In certain configurations, the one or more non-alcohol based compounds include at least one of iodine, para-chloro-meta-xylenol, bis-biguanides, chlorhexidine gluconate (CHG), chlorhexidine diacetate, a quaterium class compound, benzethonium chloride, benzalkonium chloride, chloroxylenol, triclosan, hexachlorophene, octenidine, diazolidinyl urea, methyl chloro isothiazoline, methyl isothiazoline, triclosan, and/or mixtures thereof.

In certain configurations, the antiseptic composition includes a mixture of alcohol and non-alcohol based compounds.

In certain configurations, the antiseptic composition includes CHG and an alcohol.

In certain configurations, the alcohol is isopropyl alcohol.

In certain configurations, the antiseptic composition includes about 2% (w/v) CHG and about 70% (v/v) isopropyl alcohol.

DESCRIPTION OF THE DISCLOSURE

Figure 1:
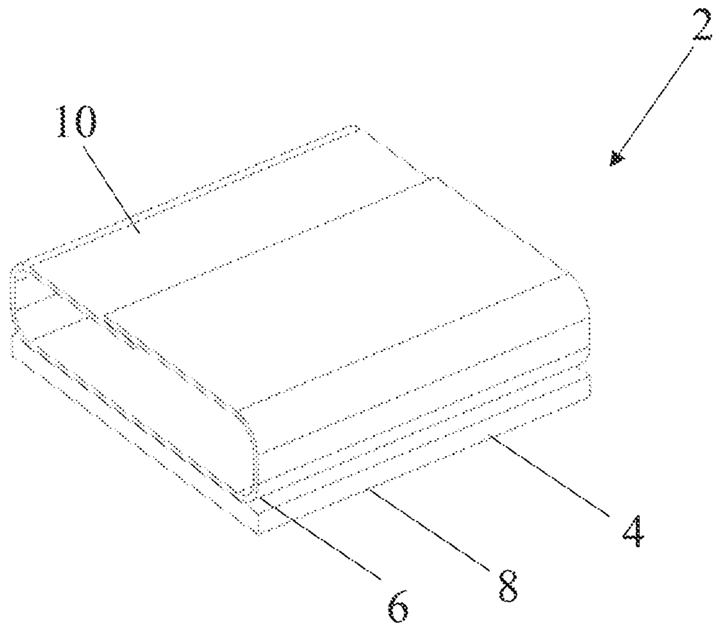
FIG. 1 is a perspective view of a skin preparation device according to a non-limiting embodiment or aspect of the present disclosure.
Figure 2:
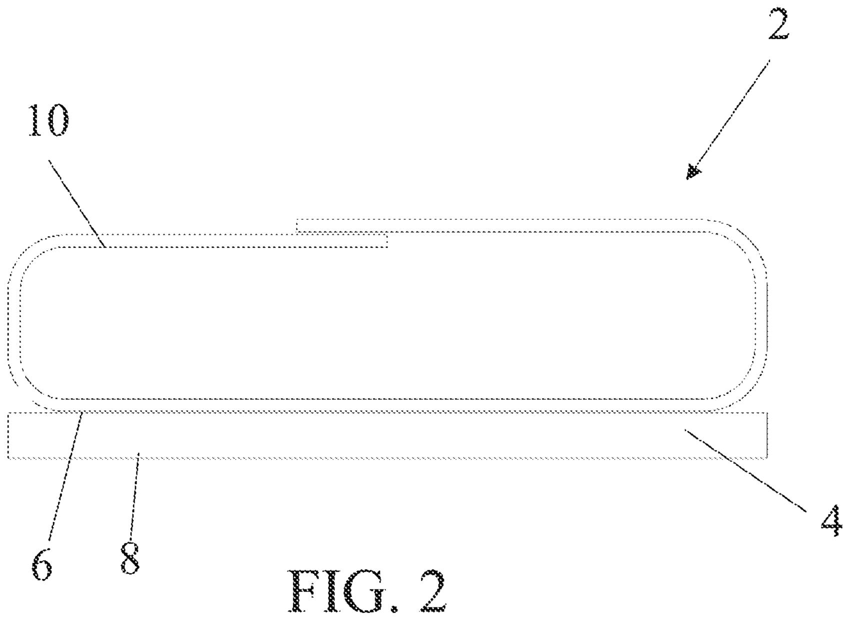
FIG. 2 is a side view of the skin preparation device of FIG. 1.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

Provided herein is a device for applying an antiseptic composition to skin of a patient, for example for preparing an area of the patient's skin for example, for injection or aspiration through skin, or a surgical intervention. As used herein, the term "patient" is any animal, including humans, and a "human patient" is any human. As used herein, the term "antiseptic composition" is any composition that prevents or inhibits the growth of one or more microorganisms on the patient's skin surface.

As used herein, the term "surgical intervention" means any percutaneous treatment (e.g., catheterization, angioplasty, needle biopsy, and the like), open surgery, laparoscopic surgery, and/or minimally-invasive surgery that involves puncturing the skin or creating one or more incisions of varying size in the skin of the patient.

In some non-limiting embodiments or aspects, as shown in FIGS. 1-4, a skin preparation device 2 according to the present disclosure is shown and described in detail. The skin preparation device 2 may include an applicator 4, such as a sponge or other porous, absorbent material that is configured to hold an antiseptic composition, and to allow a user to apply the antiseptic composition to the patient's skin at the site of the surgical intervention and, optionally, one or more areas adjacent to the site of the surgical intervention. The applicator 4 can be a natural sponge, a synthetic sponge including, for example and without limitation, a polyurethane, a polyester, and/or a vegetal cellulose, or other suitable material, so long as the material is capable of absorbing and/or dispensing the antiseptic composition. The applicator 4 may have a top surface 6 and a bottom surface 8. Either surface can be used to apply the antiseptic composition to the patient's skin; however, for simplicity, the device 2 will be described herein with reference to the bottom surface 8 as the surface that is configured to come into contact with the patient's skin. In one example, the applicator 4 may be a disinfectant wipe.

In non-limiting embodiments or aspects, the antiseptic composition includes one or more alcohols, such as ethyl alcohol, propyl alcohol, isopropyl alcohol, n-propanol, and/or mixtures thereof. In non-limiting embodiments or aspects, the antiseptic composition includes one or more non-alcohol based compounds, such as iodine, para-chloro-meta-xylenol, bis-biguanides such as chlorhexidine gluconate (CHG), chlorhexidine diacetate or quaterium class compounds such as benzethonium chloride, benzalkonium chloride, chloroxylenol, triclosan, hexachlorophenes, octenidine, diazolidinyl urea, methyl chloro isothiazoline, methyl isothiazoline, triclosan, and/or mixtures thereof. In non-limiting embodiments or aspects, the antiseptic composition includes a mixture of any of the aforementioned, including mixtures of alcohol and non-alcohol based compounds. In non-limiting embodiments or aspects, the antiseptic composition includes CHG and an alcohol, for example isopropyl alcohol. In non-limiting embodiments or aspects, the antiseptic composition includes about 2% (w/v) CHG and about 70% (v/v) isopropyl alcohol.

In non-limiting embodiments or aspects, the antiseptic composition is effective against one or more microorganisms, such as bacteria, viruses, and/or fungi. In non-limiting embodiments or aspects, the microorganism is one or more of coagulase-negative staphylococci, *Staphylococcus aureus* (including methicillin-resistant *S. aureus*), *Enterococcus* spp. (including vancomycin-resistant Enterococci, such as *E. faecium*), *Candida* spp., *Escherichia coli* (including extended-spectrum cephalosporin resistant *E. coli* and carbanpenem-resistant *E. coli*), *Clostridium difficile, Pseudomonas aeruginosa* (including carbapenem-resistant *P. aeruginosa*), *Klebsiella pneumoniae* (including extended-spectrum cephalosporin-resistant *K. pneumoniae* and carbapenem-resistant *K. pneumoniae*), *Enterobacter* spp., *Acinetobacter* spp. (including *Acinetobacter baumannii*), and *Klebsiella oxytoca.*

In non-limiting embodiments or aspects, the skin preparation device 2 may include a holding member 10 to allow a user to apply the antiseptic composition to the skin of a patient, while maintaining aseptic technique (e.g., by not directly contacting the applicator or the patient's skin surface). In one example, the holding member 10 may be a looped member that allows a user to insert his/her finger therethrough to use the skin preparation device 2 or to permit a user to grip the holding member 10 to use the skin preparation device 2. In one example, the applicator 4 and the holding member 10 may be made of the same material. The holding member 10 can be a natural sponge, a synthetic sponge including, for example and without limitation, a polyurethane, a polyester, and/or a vegetal cellulose, or other suitable material, so long as the material is capable of absorbing and/or dispensing the antiseptic composition. By using the same material for both the applicator 4 and the holding member 10, the skin preparation device 2 ensures that both the user's skin surface and the patient's skin surface are disinfected. Further, the holding member 10 will cover the user's finger(s) with the material so that, in the event the user's finger(s) touch the patient's skin surface, the material contacts the patient's skin surface instead. In one example, the holding member 10 may be a monolithic piece of material that defines a passageway therethrough to receive the user's finger(s). In another example, the holding member 10 may be a piece of material that includes ends bonded to one another to form the passageway to receive the user's finger(s). In one example of the present disclosure, the material of the holding member 10 may be thinner than the material of the applicator 4.

Figure 3:
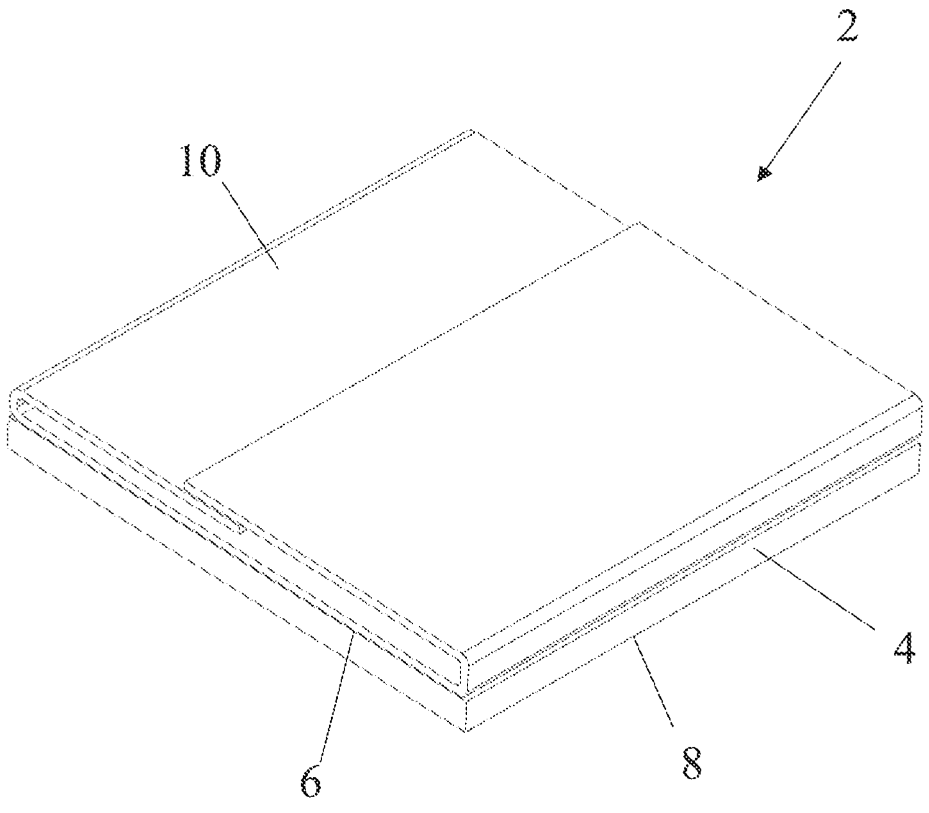
FIG. 3 is a perspective view of the skin preparation device of FIG. 1 in a compressed state.
Figure 4:
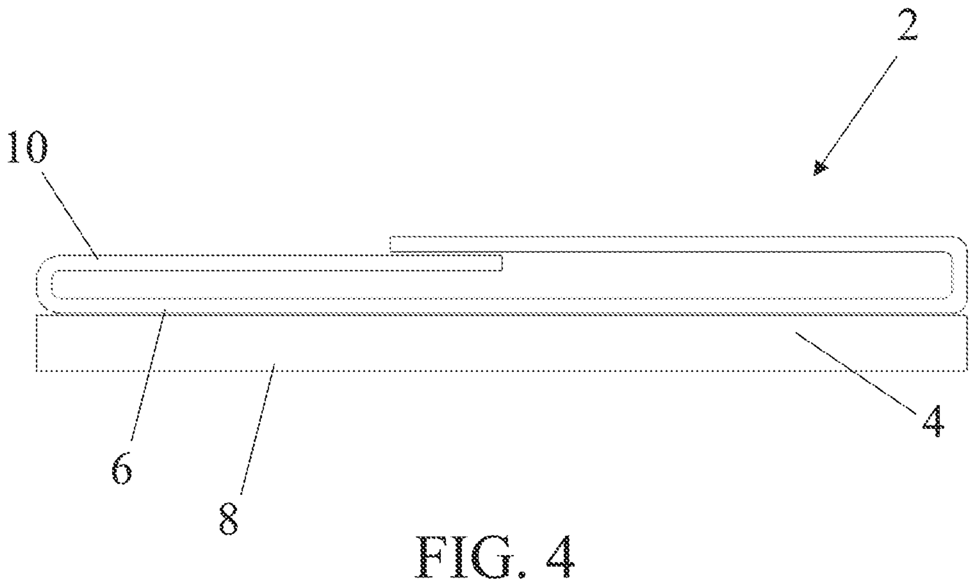
FIG. 4 is a side view of the compressed skin preparation device of FIG. 3.
Figure 5:
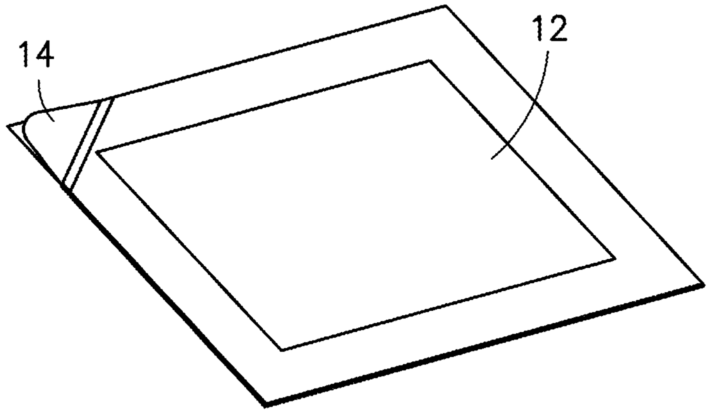
FIG. 5 is a perspective view of a packaging to hold the skin preparation device of FIG. 1 according to one non-limiting embodiment or aspect of the present disclosure.
Figure 6:
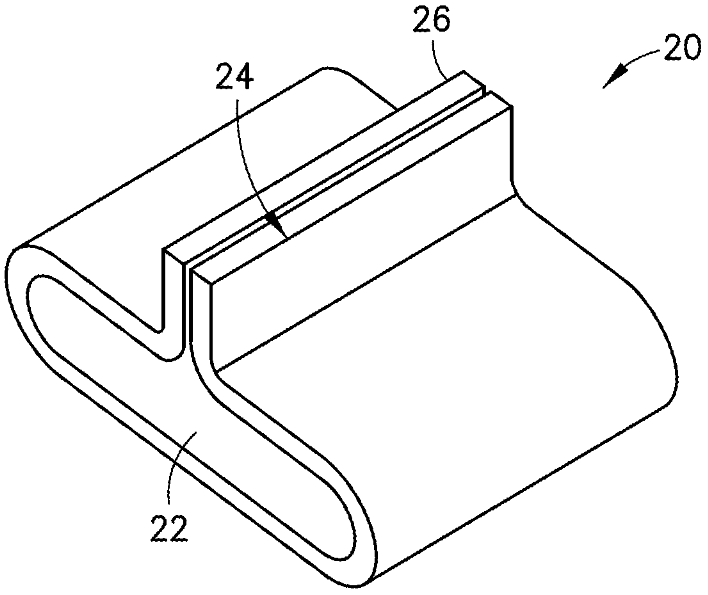
FIG. 6 is a perspective view of a skin preparation device according to a non-limiting embodiment or aspect of the present disclosure.

As shown in FIGS. 3-5, according to non-limiting embodiments or aspects of the present disclosure, the skin preparation device 2 may be provided in a packaging 12. The packaging 12 may be made of at least two pieces of material that receive the skin preparation device 2 therebetween. The packaging 12 may be opened by pulling a tab 14 that causes the two pieces of material to be pulled apart. As shown in FIG. 4, when the skin preparation device 2 is held in the packaging 12, the holding member 10 may be flattened to fit within the packaging 12. After the skin preparation device 2 has been removed from the packaging 12, the holding member 10 may spring into a use position or may be pulled in to a use position by the user so that a user may insert his/her finger through the holding member 10.

With reference to FIGS. 6-9, according to some non-limiting embodiments and aspects, a skin preparation device 20 is shown and described in detail. The skin preparation device 20 may include an applicator portion 22 and a handle portion 24. In one example, the applicator portion 22 and the handle portion 24 are formed as a monolithic structure and are formed integral with one another from a single piece of material. In other examples, the applicator portion 22 and the handle portion 24 may be two pieces of material operatively connected to one another. The applicator portion 22 and the handle portion 24 may form a ring-like structure that has a passageway defined therethrough.

The applicator portion 22 can be a natural sponge, a synthetic sponge including, for example and without limitation, a polyurethane, a polyester, and/or a vegetal cellulose, or other suitable material, so long as the material is capable of absorbing and/or dispensing the antiseptic composition. In one example, the handle portion 24 may be made of the same material as the applicator portion 22. In one example, the applicator portion 22 may be a disinfectant wipe.

In non-limiting embodiments or aspects, the antiseptic composition includes one or more alcohols, such as ethyl alcohol, propyl alcohol, isopropyl alcohol, n-propanol, and/or mixtures thereof. In non-limiting embodiments or aspects, the antiseptic composition includes one or more non-alcohol based compounds, such as iodine, para-chloro-meta-xylenol, bis-biguanides such as chlorhexidine gluconate (CHG), chlorhexidine diacetate or quaterium class compounds such as benzethonium chloride, benzalkonium chloride, chloroxylenol, triclosan, hexachlorophenes, octenidine, diazolidinyl urea, methyl chloro isothiazoline, methyl isothiazoline, triclosan, and/or mixtures thereof. In non-limiting embodiments or aspects, the antiseptic composition includes a mixture of any of the aforementioned, including mixtures of alcohol and non-alcohol based compounds. In non-limiting embodiments or aspects, the antiseptic composition includes CHG and an alcohol, for example isopropyl alcohol. In non-limiting embodiments or aspects, the antiseptic composition includes about 2% (w/v) CHG and about 70% (v/v) isopropyl alcohol.

In non-limiting embodiments or aspects, the antiseptic composition is effective against one or more microorganisms, such as bacteria, viruses, and/or fungi. In non-limiting embodiments or aspects, the microorganism is one or more of coagulase-negative staphylococci, *Staphylococcus aureus* (including methicillin-resistant *S. aureus*), *Enterococcus* spp. (including vancomycin-resistant Enterococci, such as *E. faecium*), *Candida* spp., *Escherichia coli* (including extended-spectrum cephalosporin resistant *E. coli* and carbanpenem-resistant *E. coli*), *Clostridium difficile, Pseudomonas aeruginosa* (including carbapenem-resistant *P. aeruginosa*), *Klebsiella pneumoniae* (including extended-spectrum cephalosporin-resistant *K. pneumoniae* and carbapenem-resistant *K. pneumoniae*), *Enterobacter* spp., *Acinetobacter* spp. (including *Acinetobacter baumannii*), and *Klebsiella oxytoca.*

Figure 7:
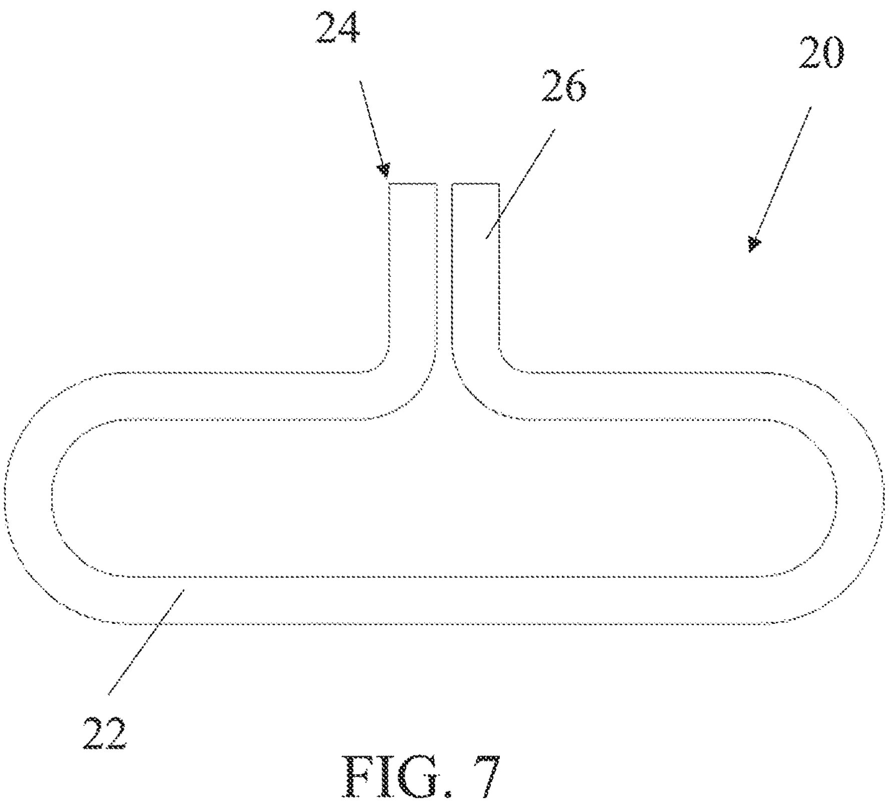
FIG. 7 is a side view of the skin preparation device of FIG. 6.
Figure 8:
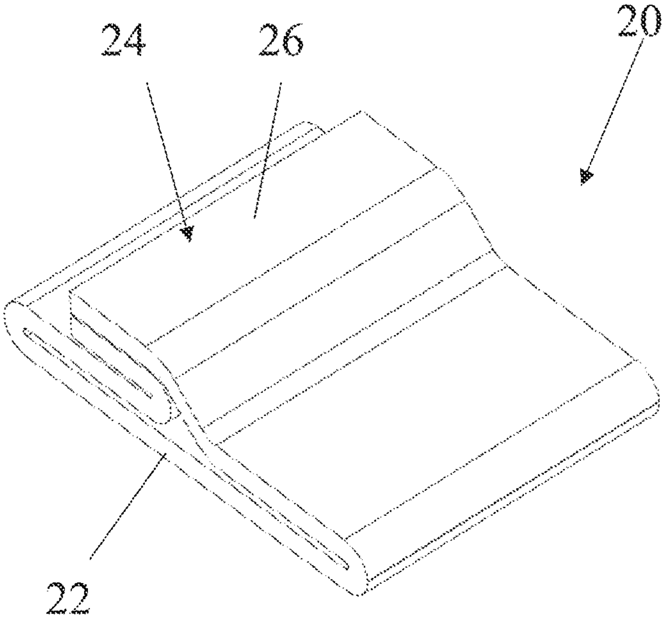
FIG. 8 is a perspective view of the skin preparation device of FIG. 6 in a compressed state.
Figure 9:
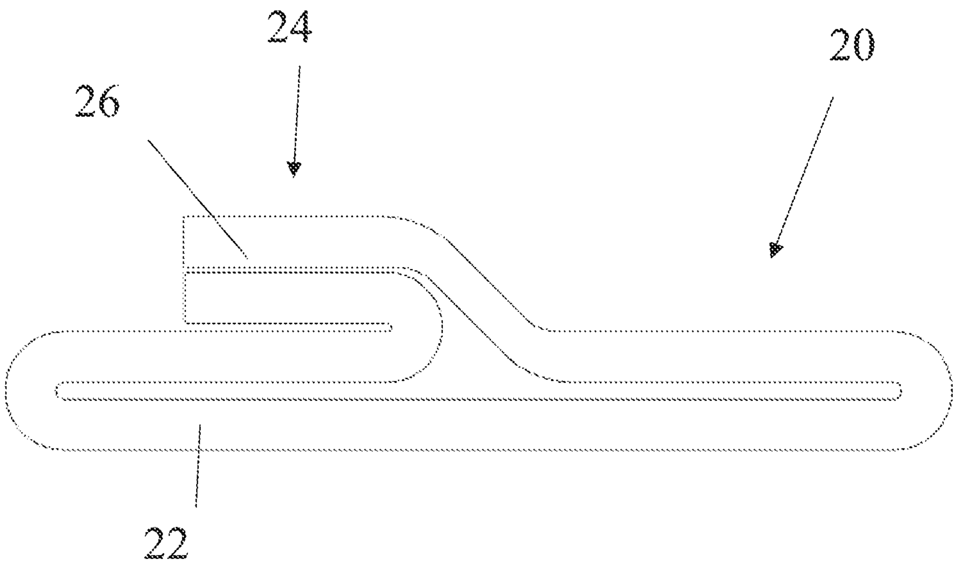
FIG. 9 is a side view of the compressed skin preparation device of FIG. 8.
Figure 10:
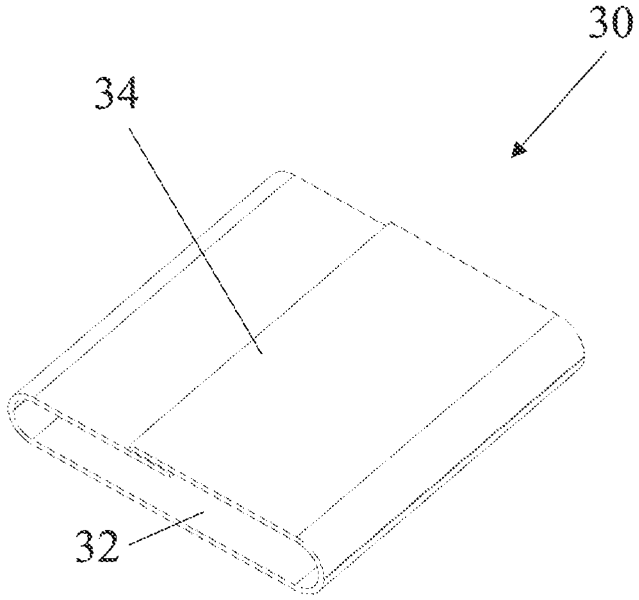
FIG. 10 is a perspective view of a skin preparation device according to a non-limiting embodiment or aspect of the present disclosure.

In some non-limiting embodiments and aspects, the handle portion 24 may include the two opposing ends of the skin preparation device 20. The handle portion 24 may bend upwardly from the applicator portion 22 to form gripping portions for the user to grasp when using the skin preparation device 20. In one example, the opposing ends of the skin preparation device 20 may be bonded together to form the handle portion 24. In some examples, the opposing ends of the skin preparation device 20 may be adhesively bonded or heat bonded. In order to signify to the user the location of the handle portion 24, the handle portion 24 may be colored differently from the applicator portion 22. In another example, the handle portion 24 may include written instructions or pictorials to indicate to the user that the handle portion 24 should be grasped. As shown in FIGS. 7 and 9, in some non-limiting embodiments or aspects, the handle portion 24 may be folded over the applicator portion 22 when held in a packaging (not shown) to reduce the overall size of the skin preparation device 20 when held in the packaging. When in use, the user may squeeze the handle portion 24 between his/her thumb and index finger to grip the skin preparation device 20.

With reference to FIGS. 10-13, according to some non-limiting embodiments and aspects, a skin preparation device 30 is shown and described in detail. The skin preparation device 30 may include an applicator portion 32 and a clasping portion 34. In one example, the applicator portion 32 and the clasping portion 34 are formed as a monolithic structure and are formed integral with one another from a single piece of material. In other examples, the applicator portion 32 and the clasping portion 34 may be two pieces of material operatively connected to one another. In some examples, the opposing ends of the skin preparation device 30 may be adhesively bonded or heat bonded together. The applicator portion 32 and the clasping portion 34 may form a ring-like structure that has a passageway defined therethrough, in which the user can insert his/her finger to use the skin preparation device 30.

The applicator portion 32 can be a natural sponge, a synthetic sponge including, for example and without limitation, a polyurethane, a polyester, and/or a vegetal cellulose, or other suitable material, so long as the material is capable of absorbing and/or dispensing the antiseptic composition. In one example, the clasping portion 34 may be made of the same material as the applicator portion 32. In one example, the applicator portion 32 may be a disinfectant wipe.

In non-limiting embodiments or aspects, the antiseptic composition includes one or more alcohols, such as ethyl alcohol, propyl alcohol, isopropyl alcohol, n-propanol, and/or mixtures thereof. In non-limiting embodiments or aspects, the antiseptic composition includes one or more non-alcohol based compounds, such as iodine, para-chloro-meta-xylenol, bis-biguanides such as chlorhexidine gluconate (CHG), chlorhexidine diacetate or quaterium class compounds such as benzethonium chloride, benzalkonium chloride, chloroxylenol, triclosan, hexachlorophenes, octenidine, diazolidinyl urea, methyl chloro isothiazoline, methyl isothiazoline, triclosan, and/or mixtures thereof. In non-limiting embodiments or aspects, the antiseptic composition includes a mixture of any of the aforementioned, including mixtures of alcohol and non-alcohol based compounds. In non-limiting embodiments or aspects, the antiseptic composition includes CHG and an alcohol, for example isopropyl alcohol. In non-limiting embodiments or aspects, the antiseptic composition includes about 2% (w/v) CHG and about 70% (v/v) isopropyl alcohol.

In non-limiting embodiments or aspects, the antiseptic composition is effective against one or more microorganisms, such as bacteria, viruses, and/or fungi. In non-limiting embodiments or aspects, the microorganism is one or more of coagulase-negative staphylococci, *Staphylococcus aureus* (including methicillin-resistant *S. aureus*), *Enterococcus* spp. (including vancomycin-resistant Enterococci, such as *E. faecium*), *Candida* spp., *Escherichia coli* (including extended-spectrum cephalosporin resistant *E. coli* and carbanpenem-resistant *E. coli*), *Clostridium difficile, Pseudomonas aeruginosa* (including carbapenem-resistant *P. aeruginosa*), *Klebsiella pneumoniae* (including extended-spectrum cephalosporin-resistant *K. pneumoniae* and carbapenem-resistant *K. pneumoniae*), *Enterobacter* spp., *Acinetobacter* spp. (including *Acinetobacter baumannii*), and *Klebsiella oxytoca.*

Figure 11:
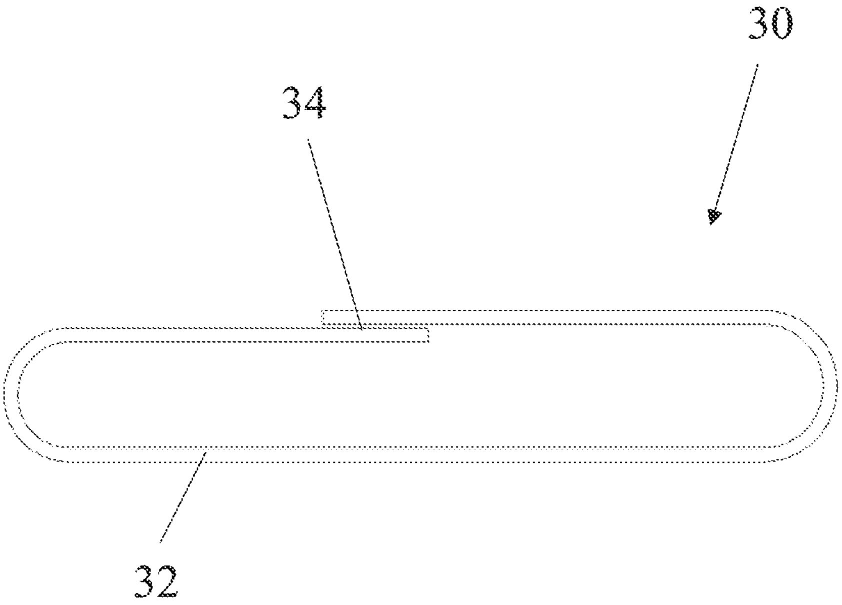
FIG. 11 is a side view of the skin preparation device of FIG. 10.
Figure 12:
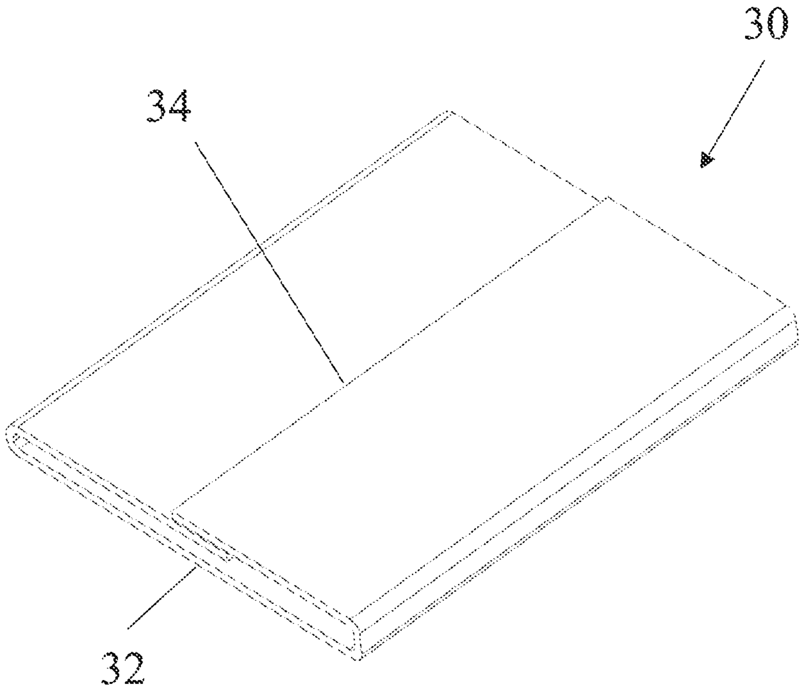
FIG. 12 is a perspective view of the skin preparation device of FIG. 10 in a compressed state.
Figure 13:
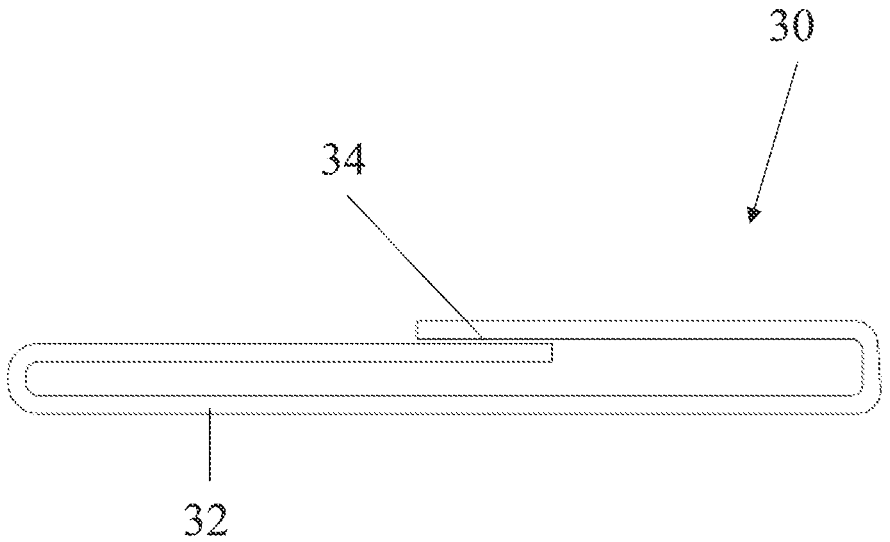
FIG. 13 is a side view of the compressed skin preparation device of FIG. 12.
Figure 14:
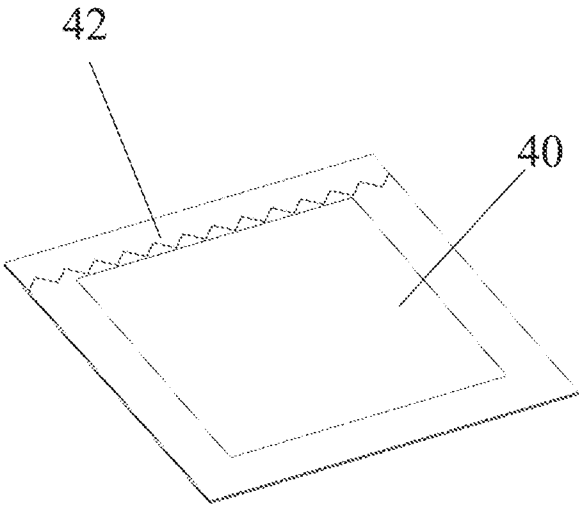
FIG. 14 is a perspective view of a packaging for holding a skin preparation device according to a non-limiting embodiment or aspect of the present disclosure.

In one example, the opposing ends of the skin preparation device 30 may be bonded together to form the clasping portion 34. As shown in FIGS. 11 and 13, according to some non-limiting embodiments or aspects, the skin preparation device 30 may be folded to deflate the ring-like structure to reduce the overall size of the skin preparation device 30 when packaging the skin preparation device 30.

With reference to FIGS. 14-19, according to some non-limiting embodiments and aspects, a packaging 40 for the skin preparation device 20 is shown and described. The packaging 40 may define a cavity to receive the skin preparation device 20. A tear-off portion 42 may be provided on one end of the packaging 40 to permit a user to tear off a portion of the packaging 40 to remove the skin preparation device 20 therefrom. The tear-off portion 42 may be precut to allow for an easier removal of the tear-off portion 42 from the packaging 40.

Figure 15:
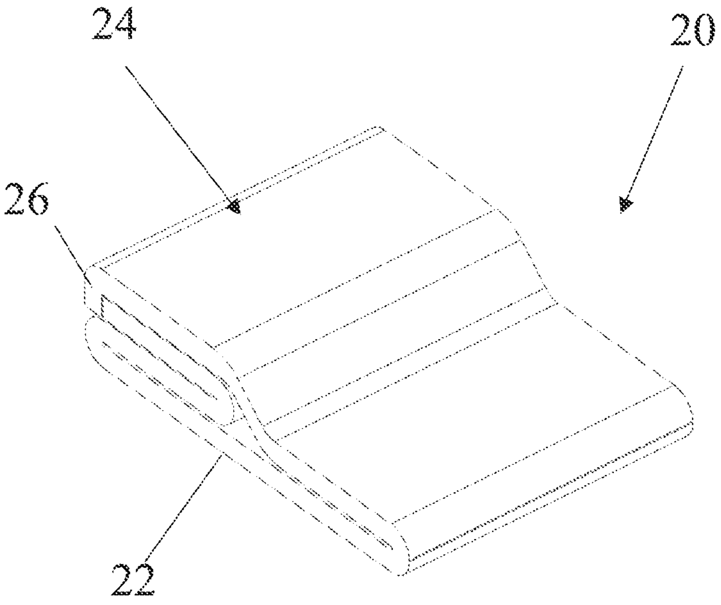
FIG. 15 is a perspective view of the skin preparation device of FIG. 6 with a tip of a holding portion bent over.
Figure 16:
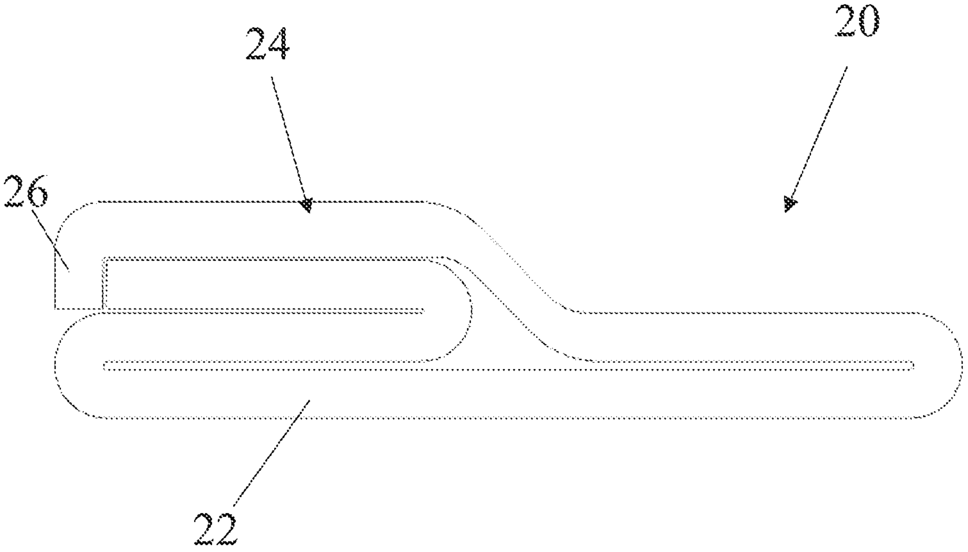
FIG. 16 is a side view of the compressed skin preparation device of FIG. 15.
Figure 17:
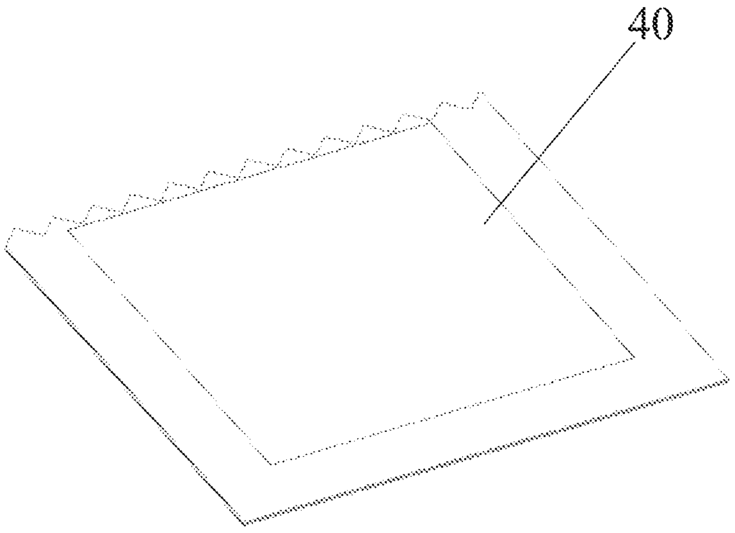
FIG. 17 is a perspective view of the packaging of FIG. 14 with a tear-off portion removed.
Figure 18:
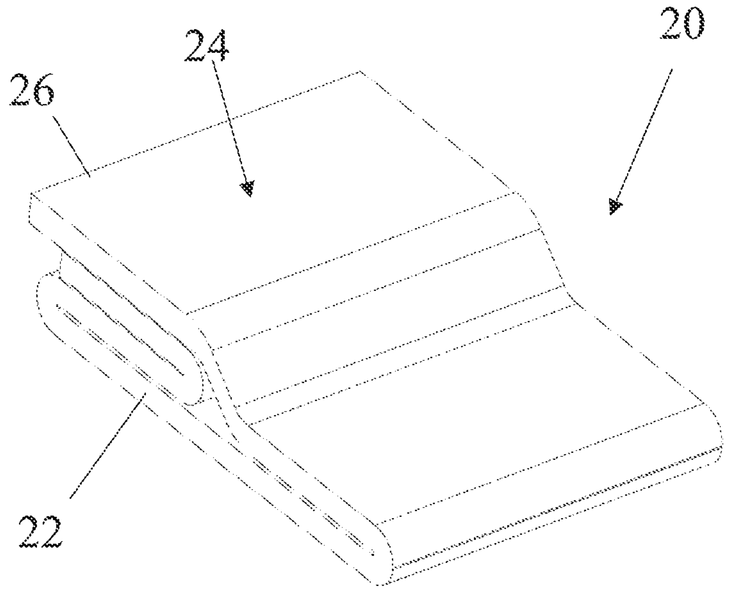
FIG. 18 is a perspective view of the skin preparation device of FIG. 6 with the tip of the holding portion extended.
Figure 19:
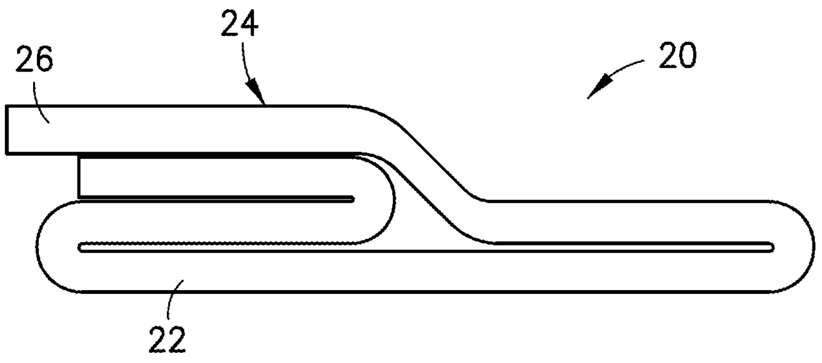
FIG. 19 is a side view of the extended skin preparation device of FIG. 18.
Figure 20:
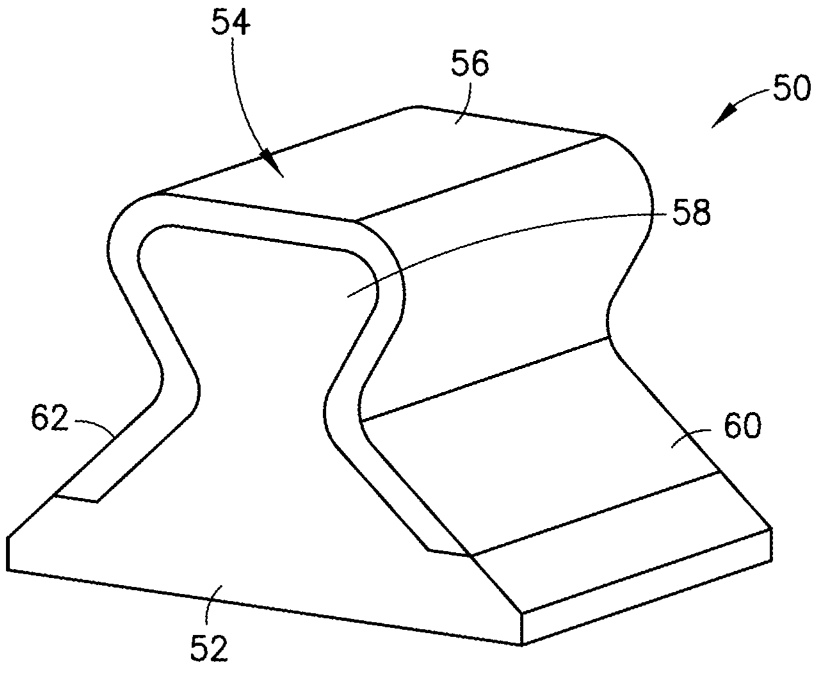
FIG. 20 is a perspective view of a skin preparation device according to one non-limiting embodiment or aspect of the present disclosure.
Figure 21:
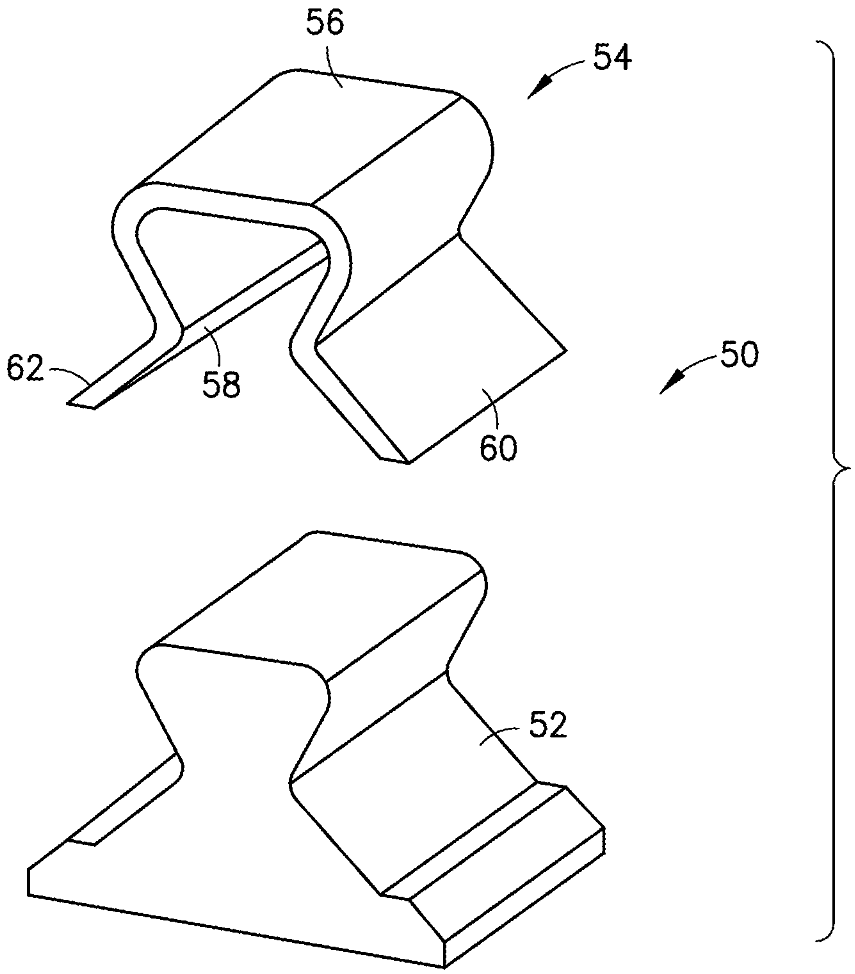
FIG. 21 is an exploded view of the skin preparation device of FIG. 20.

As shown in FIGS. 15 and 16, according to some non-limiting embodiments or aspects, the handle portion 24 of the skin preparation device 20 may be folded over onto the applicator portion 22 to reduce the overall size of the skin preparation device 20. The handle portion 24 may be folded towards the tear-off portion 42 of the packaging 40 so that, after the tear-off portion 42 has been removed, the user may grip the handle portion 24 and pull the skin preparation device 20 from the packaging 40 without contaminating the applicator portion 22. In one example, a tip 26 of the handle portion 24 may be bent over the remaining portion of the handle portion 24. After the tear-off portion 42 has been removed from the packaging 40, the tip 26 may flex away from the handle portion 24 and out of the packaging 40 for easy gripping by the user.

With reference to FIGS. 20-24, according to a non-limiting embodiment or aspect of the present disclosure, a skin preparation device 50 is shown and described in detail. The skin preparation device 50 may include an applicator 52 and a holding portion 54. In one example, the holding portion 54 is configured to receive the applicator 52.

The applicator 52 can be a natural sponge, a synthetic sponge including, for example and without limitation, a polyurethane, a polyester, and/or a vegetal cellulose, or other suitable material, so long as the material is capable of absorbing and/or dispensing the antiseptic composition.

In non-limiting embodiments or aspects, the antiseptic composition includes one or more alcohols, such as ethyl alcohol, propyl alcohol, isopropyl alcohol, n-propanol, and/or mixtures thereof. In non-limiting embodiments or aspects, the antiseptic composition includes one or more non-alcohol based compounds, such as iodine, para-chloro-meta-xylenol, bis-biguanides such as chlorhexidine gluconate (CHG), chlorhexidine diacetate or quaterium class compounds such as benzethonium chloride, benzalkonium chloride, chloroxylenol, triclosan, hexachlorophenes, octenidine, diazolidinyl urea, methyl chloro isothiazoline, methyl isothiazoline, triclosan, and/or mixtures thereof. In non-limiting embodiments or aspects, the antiseptic composition includes a mixture of any of the aforementioned, including mixtures of alcohol and non-alcohol based compounds. In non-limiting embodiments or aspects, the antiseptic composition includes CHG and an alcohol, for example isopropyl alcohol. In non-limiting embodiments or aspects, the antiseptic composition includes about 2% (w/v) CHG and about 70% (v/v) isopropyl alcohol.

In non-limiting embodiments or aspects, the antiseptic composition is effective against one or more microorganisms, such as bacteria, viruses, and/or fungi. In non-limiting embodiments or aspects, the microorganism is one or more of coagulase-negative staphylococci, *Staphylococcus aureus* (including methicillin-resistant *S. aureus*), *Enterococcus* spp. (including vancomycin-resistant Enterococci, such as *E. faecium*), *Candida* spp., *Escherichia coli* (including extended-spectrum cephalosporin resistant *E. coli* and carbanpenem-resistant *E. coli*), *Clostridium difficile, Pseudomonas aeruginosa* (including carbapenem-resistant *P. aeruginosa*), *Klebsiella pneumoniae* (including extended-spectrum cephalosporin-resistant *K. pneumoniae* and carbapenem-resistant *K. pneumoniae*), *Enterobacter* spp., *Acinetobacter* spp. (including *Acinetobacter baumannii*), and *Klebsiella oxytoca.*

In one non-limiting embodiment or aspect, the holding portion 54 may include a base member 56 that defines a cavity 58 to receive at least a portion of the applicator 52 and at least two reinforcing members 60, 62 that extend from the base member 56. In one example, the cavity 58 may have a round cross-sectional shape that corresponds to a round cross-sectional shape of a portion of the applicator 52. The applicator 52 may be held in the holding portion 54 using a friction fit, using an adhesive, by welding, or by any other methods of operatively connecting two components. In one non-limiting embodiment or aspect, the applicator 52 may be made of a material different from the material used to make the holding portion 54. In one example, the applicator 52 may be a sponge material, such as Polyester Polyurethane Foam Z-100ME, and the holding portion 54 may be a plastic. In one example, the holding portion 54 may be made of a rigid plastic that supports the applicator 52. In one example, the holding portion 54 is made of Polyethylene-CPChem Marlex 9018. In one example, the holding portion 54 may be a different color than the applicator 52 to signal to a user that the holding portion 54 should be gripped instead of the applicator 52. In one example, the holding portion 54 may include written instructions or pictorials to indicate to the user that the holding portion 54 should be gripped instead of the applicator 52.

During use of the skin preparation device 50, a user may grip the holding portion 54 to press the applicator 52 against a patient's skin to apply the antiseptic composition to a surgical area on the patient's skin. By gripping the holding portion 54, the user may not contact the applicator 52 or the patient's skin surface. The reinforcing members 60, 62 may also act as guards that prevent the user's fingers from contacting the applicator 52 when gripping the skin preparation device 50 to maintain the sterility of the applicator 52.

Figure 22:
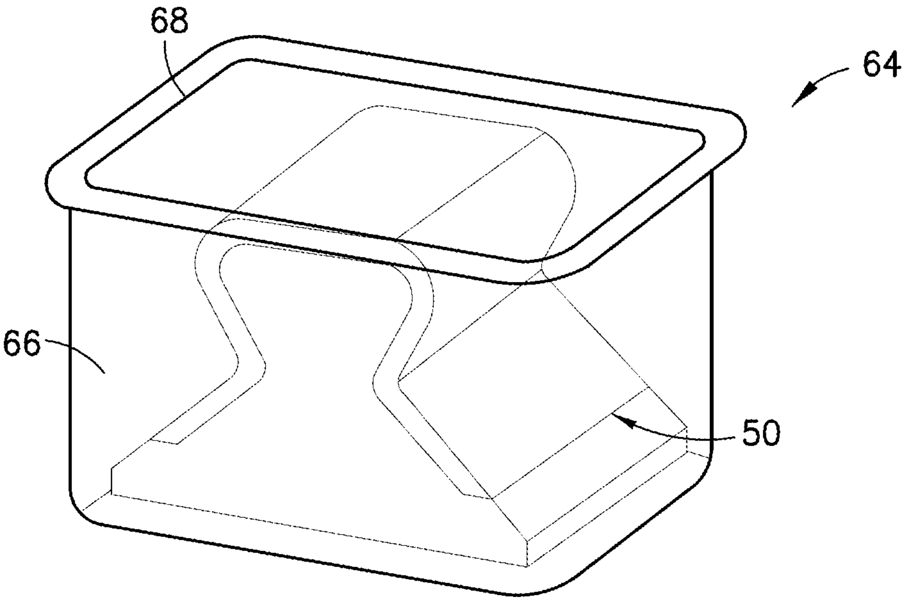
FIG. 22 is a perspective view of the skin preparation device of FIG. 20 in a packaging.
Figure 23:
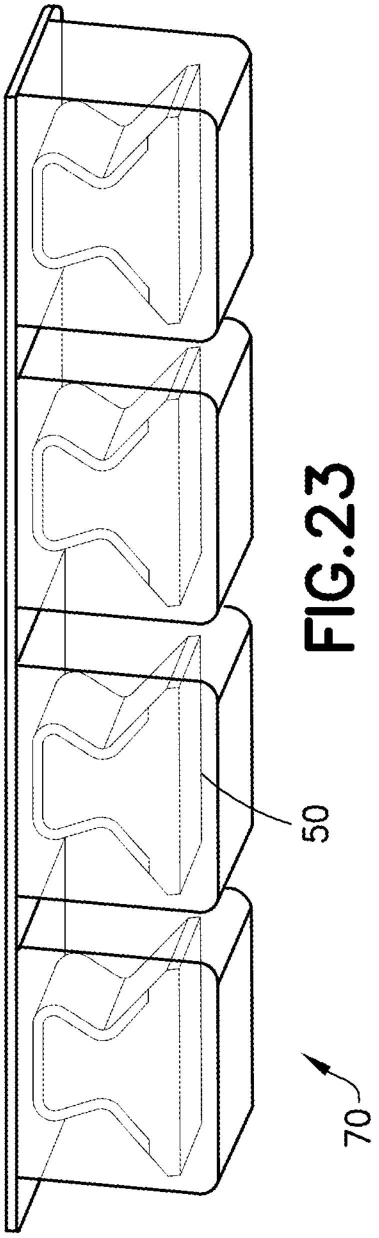
FIG. 23 is a perspective view of a strip of packages holding a plurality of skin preparation devices shown in FIG. 20.
Figure 24:
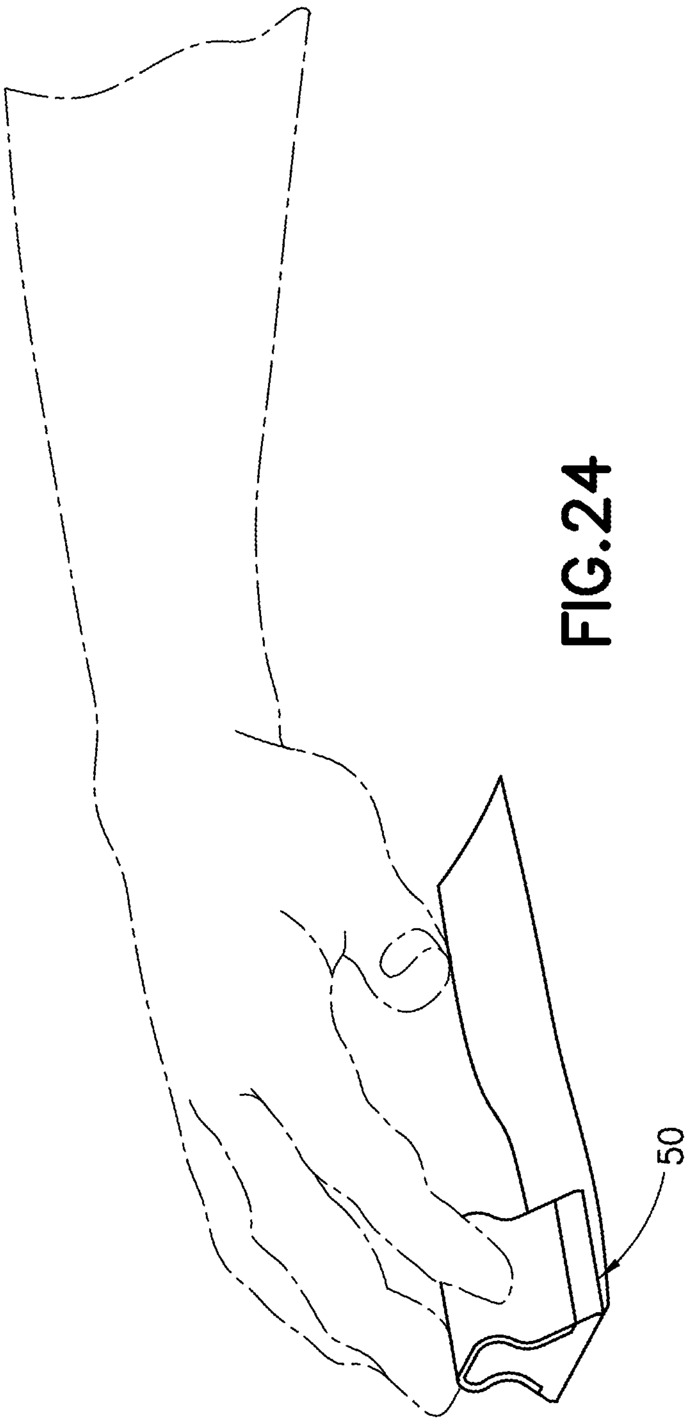
FIG. 24 is a perspective view of a user's hand gripping the skin preparation device of FIG. 20.

With reference to FIGS. 22 and 23, according to some non-limiting embodiments or aspects, the skin preparation device 50 may be stored in a packaging 64. In one example, the packaging 64 may be a blister pack. The packaging 64 may include a body 66 to receive and store the skin preparation device 50 and a removable lid 68 that seals the body 66 to keep the skin preparation device 50 sterile before use. The lid 68 may be peeled off of the body 66 to open the packaging 64 to remove the skin preparation device 50 therefrom. In one non-limiting embodiment or aspect, a plurality of blister packs may be connected together to form a strip 70 of blister packs that holds a plurality of skin preparation devices 50.

Figure 25:
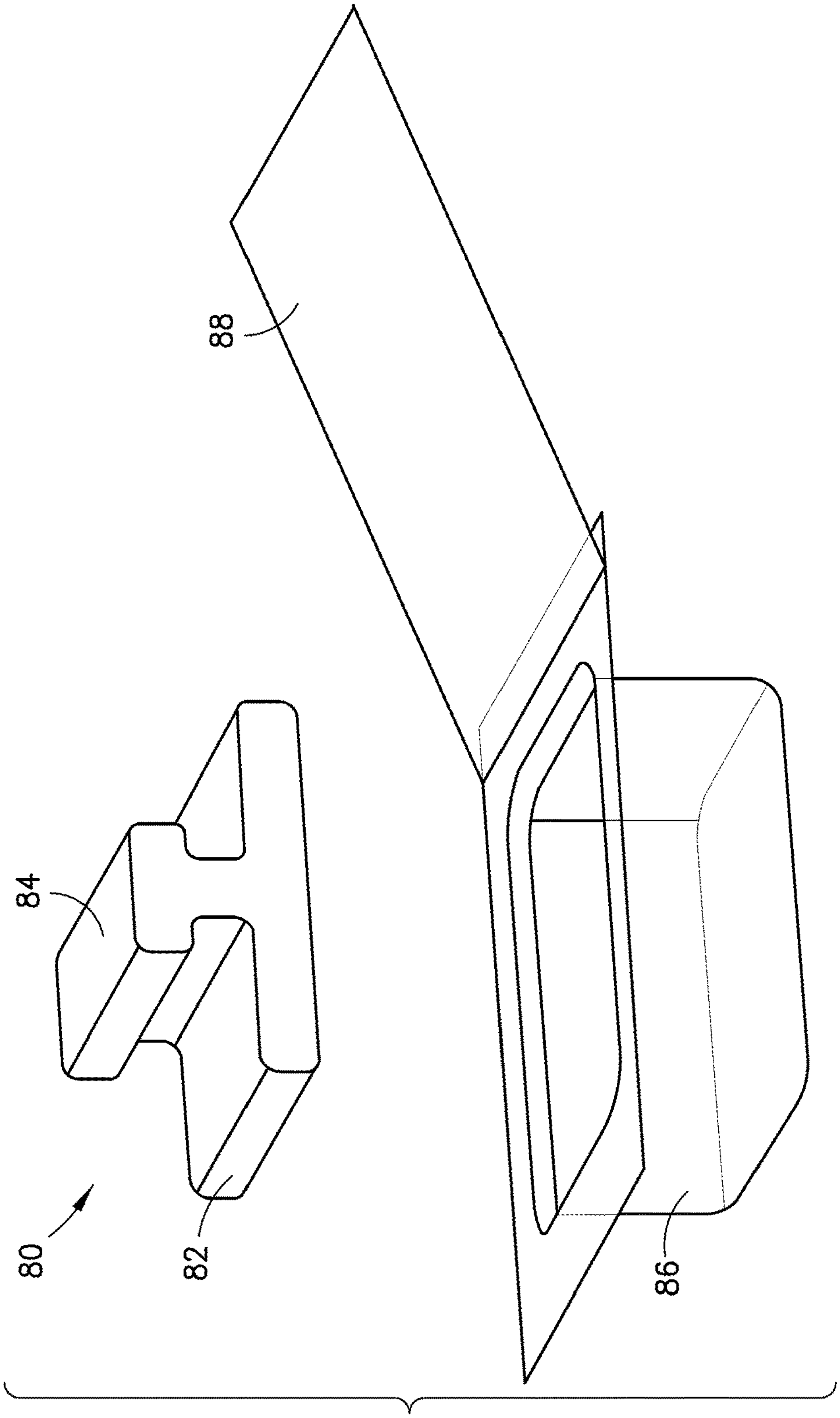
FIG. 25 is perspective view of a skin preparation device according to a non-limiting embodiment or aspect of the present disclosure.
Figure 26:
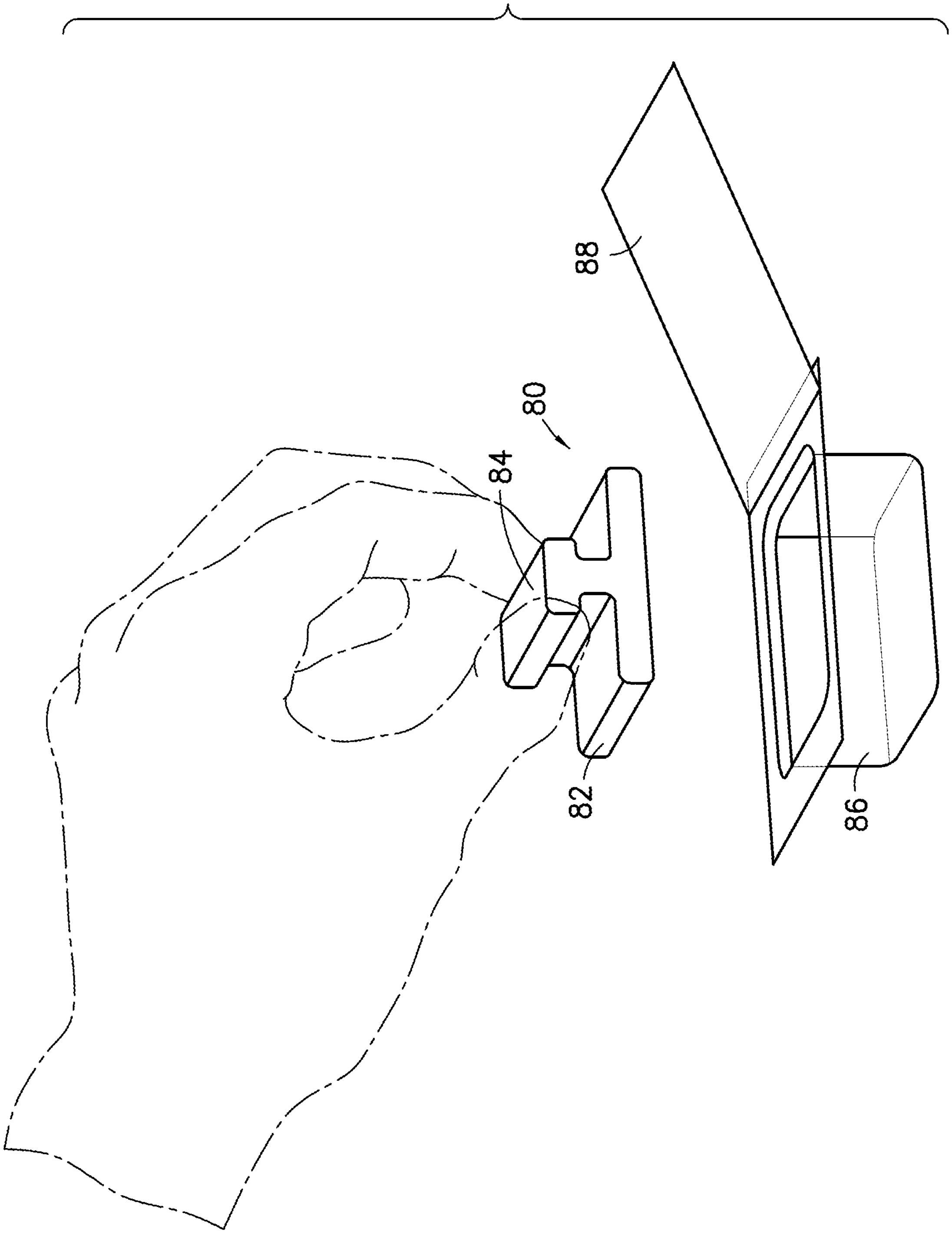
FIG. 26 is a perspective view of the skin preparation device of FIG. 25 being held by a user.
Figure 27:
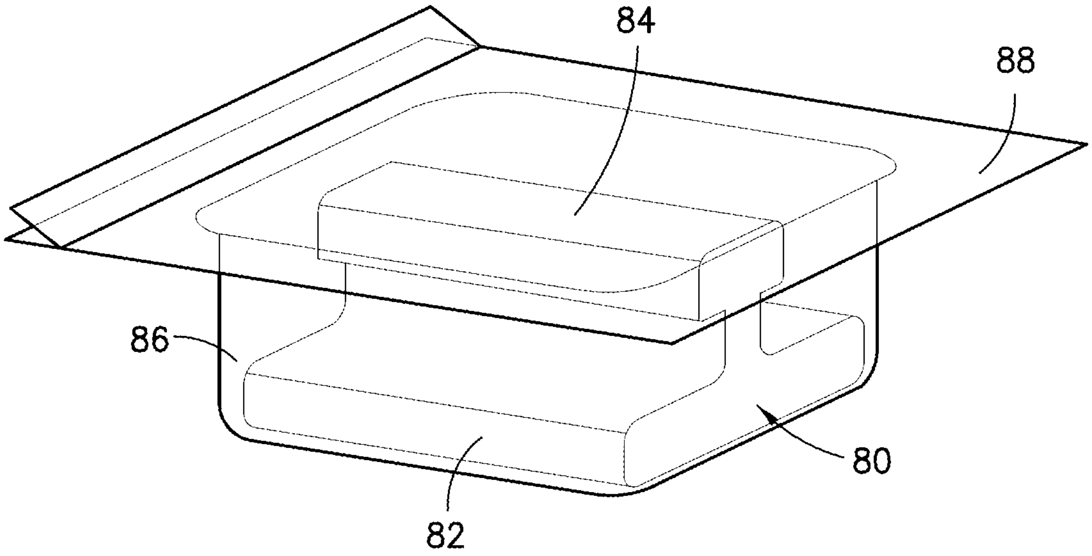
FIG. 27 is a perspective view of the skin preparation device of FIG. 25 held in a packaging.

With reference to FIGS. 25-27, according to a non-limiting embodiment or aspect of the present disclosure, a skin preparation device 80 is shown and described in detail. The skin preparation device 80 may include an applicator 82 and a holding portion 84. In one example, the applicator 82 and the holding portion 84 are formed as a monolithic structure. In one example, the applicator 82 and the holding portion 84 are made of the same material.

The applicator 82 can be a natural sponge, a synthetic sponge including, for example and without limitation, a polyurethane, a polyester, and/or a vegetal cellulose, or other suitable material, so long as the material is capable of absorbing and/or dispensing the antiseptic composition.

In non-limiting embodiments or aspects, the antiseptic composition includes one or more alcohols, such as ethyl alcohol, propyl alcohol, isopropyl alcohol, n-propanol, and/or mixtures thereof. In non-limiting embodiments or aspects, the antiseptic composition includes one or more non-alcohol based compounds, such as iodine, para-chloro-meta-xylenol, bis-biguanides such as chlorhexidine gluconate (CHG), chlorhexidine diacetate or quaterium class compounds such as benzethonium chloride, benzalkonium chloride, chloroxylenol, triclosan, hexachlorophenes, octenidine, diazolidinyl urea, methyl chloro isothiazoline, methyl isothiazoline, triclosan, and/or mixtures thereof. In non-limiting embodiments or aspects, the antiseptic composition includes a mixture of any of the aforementioned, including mixtures of alcohol and non-alcohol based compounds. In non-limiting embodiments or aspects, the antiseptic composition includes CHG and an alcohol, for example isopropyl alcohol. In non-limiting embodiments or aspects, the antiseptic composition includes about 2% (w/v) CHG and about 70% (v/v) isopropyl alcohol.

In non-limiting embodiments or aspects, the antiseptic composition is effective against one or more microorganisms, such as bacteria, viruses, and/or fungi. In non-limiting embodiments or aspects, the microorganism is one or more of coagulase-negative staphylococci, *Staphylococcus aureus* (including methicillin-resistant *S. aureus*), *Enterococcus* spp. (including vancomycin-resistant Enterococci, such as *E. faecium*), *Candida* spp., *Escherichia coli* (including extended-spectrum cephalosporin resistant *E. coli* and carbanpenem-resistant *E. coli*), *Clostridium difficile, Pseudomonas aeruginosa* (including carbapenem-resistant *P. aeruginosa*), *Klebsiella pneumoniae* (including extended-spectrum cephalosporin-resistant *K. pneumoniae* and carbapenem-resistant *K. pneumoniae*), *Enterobacter* spp., *Acinetobacter* spp. (including *Acinetobacter baumannii*), and *Klebsiella oxytoca.*

In one non-limiting embodiment or aspect, the holding portion 84 may be a T-shaped member that permits a user to grip the holding portion 84 to press the skin preparation device 80 against a patient's skin surface. As shown in FIG. 27, in one example, the skin preparation device 80 may be stored in a packaging 86 that includes a removable lid 88 to seal the packaging 86 to maintain a sterility of the skin preparation device 80 before use.

Figure 28:
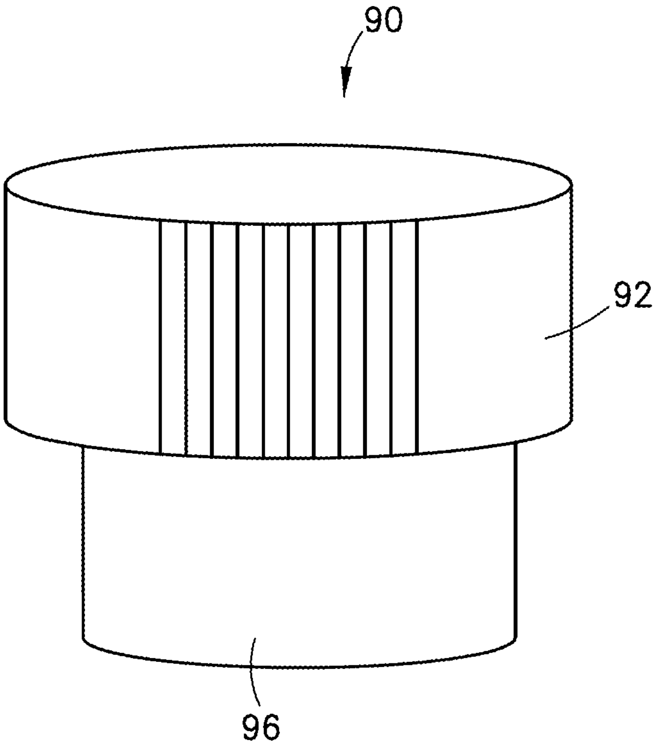
FIG. 28 is a perspective view of a skin preparation device according to one non-limiting embodiment or aspect of the present disclosure.
Figure 29:
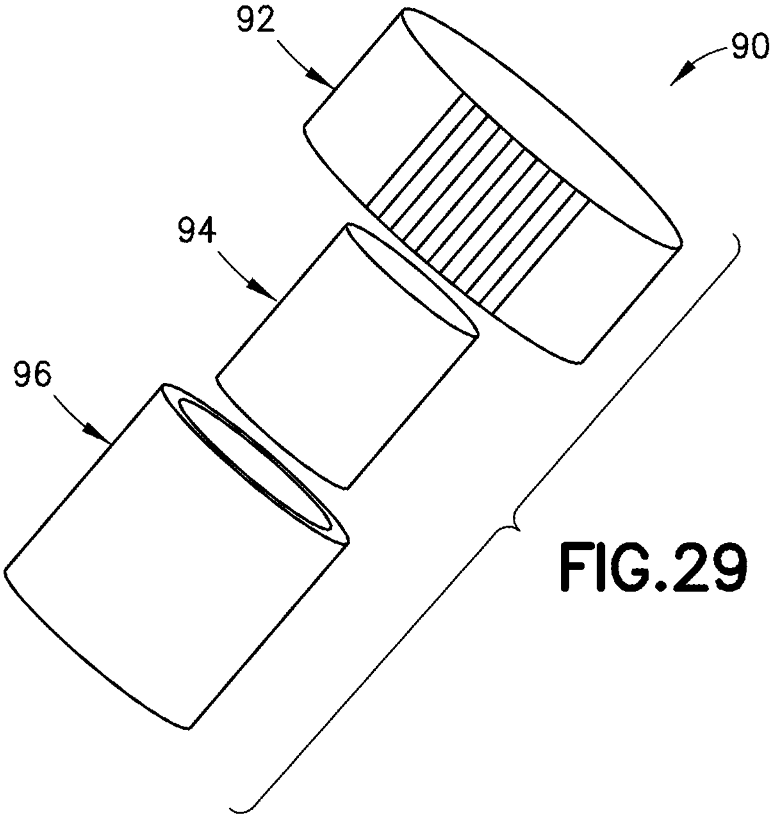
FIG. 29 is an exploded view of the skin preparation device of FIG. 28.
Figure 30:
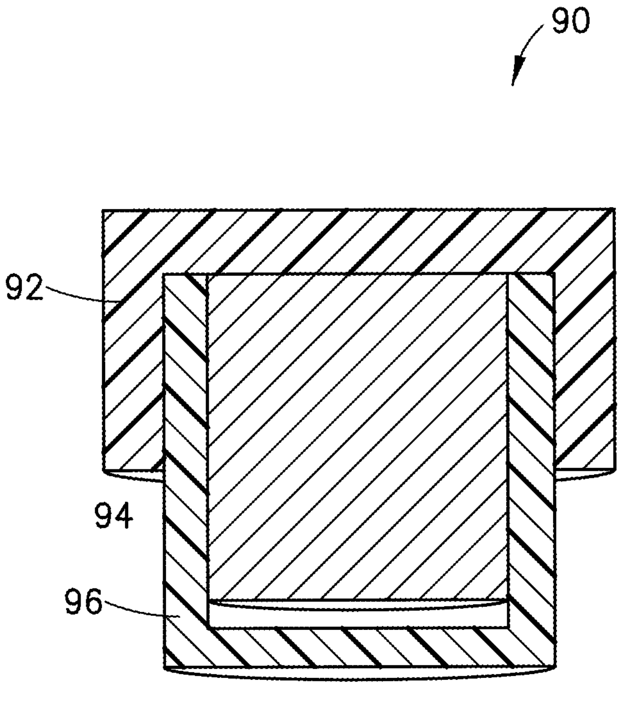
FIG. 30 is a cross-sectional view of the skin preparation device of FIG. 28.

With reference to FIGS. 28-30, according to one non-limiting embodiment or aspect, a skin preparation device 90 is shown and described in detail. The skin preparation device 90 may include a cap 92, an applicator 94, and a barrel 96. The applicator 94 may be operatively connected to the cap 92. In one example, the applicator 94 may be attached to the cap 92 using a fixing agent, such as a primer. The cap 92 may define a cavity that receives a portion of the applicator 94. A portion of the applicator 94 also extends away from the cap 92 to permit a user to press the applicator 94 against a patient's skin surface.

The applicator 94 can be a natural sponge, a synthetic sponge including, for example and without limitation, a polyurethane, a polyester, and/or a vegetal cellulose, or other suitable material, so long as the material is capable of absorbing and/or dispensing the antiseptic composition.

In non-limiting embodiments or aspects, the antiseptic composition includes one or more alcohols, such as ethyl alcohol, propyl alcohol, isopropyl alcohol, n-propanol, and/or mixtures thereof. In non-limiting embodiments or aspects, the antiseptic composition includes one or more non-alcohol based compounds, such as iodine, para-chloro-meta-xylenol, bis-biguanides such as chlorhexidine gluconate (CHG), chlorhexidine diacetate or quaterium class compounds such as benzethonium chloride, benzalkonium chloride, chloroxylenol, triclosan, hexachlorophenes, octenidine, diazolidinyl urea, methyl chloro isothiazoline, methyl isothiazoline, triclosan, and/or mixtures thereof. In non-limiting embodiments or aspects, the antiseptic composition includes a mixture of any of the aforementioned, including mixtures of alcohol and non-alcohol based compounds. In non-limiting embodiments or aspects, the antiseptic composition includes CHG and an alcohol, for example isopropyl alcohol. In non-limiting embodiments or aspects, the antiseptic composition includes about 2% (w/v) CHG and about 70% (v/v) isopropyl alcohol.

In non-limiting embodiments or aspects, the antiseptic composition is effective against one or more microorganisms, such as bacteria, viruses, and/or fungi. In non-limiting embodiments or aspects, the microorganism is one or more of coagulase-negative staphylococci, *Staphylococcus aureus* (including methicillin-resistant *S. aureus*), *Enterococcus* spp. (including vancomycin-resistant Enterococci, such as *E. faecium*), *Candida* spp., *Escherichia coli* (including extended-spectrum cephalosporin resistant *E. coli* and carbanpenem-resistant *E. coli*), *Clostridium difficile, Pseudomonas aeruginosa* (including carbapenem-resistant *P. aeruginosa*), *Klebsiella pneumoniae* (including extended-spectrum cephalosporin-resistant *K. pneumoniae* and carbapenem-resistant *K. pneumoniae*), *Enterobacter* spp., *Acinetobacter* spp. (including *Acinetobacter baumannii*), and *Klebsiella oxytoca.*

The antiseptic composition may be directly applied to the applicator 94 before insertion into the barrel 96 or the antiseptic composition may be held in the barrel 96 and the applicator 94 is dipped or inserted into the barrel 96 to soak in the antiseptic composition. After the antiseptic composition has been applied to the applicator 94, the cap 92 may be locked to the barrel 96. In one example, the cap 92 may include a helical locking thread on an inner surface thereof and the barrel 96 may have a corresponding helical locking thread on an exterior surface thereof so that the cap 92 can be rotated into a locking position on the barrel 96. In one example, the cap 92 seals to the barrel 96 to maintain the sterility of the applicator 94 and the antiseptic composition held in the barrel 96. In one example, a shape of the applicator 94 corresponds to a shape of a cavity defined by the barrel 96 so that the applicator 94 can be inserted into the barrel 96.

When using the skin preparation device 90, a user may grip the outer surface of the cap 92 and twist the cap 92 to remove the cap 92 from the barrel 96. Once the cap 92 is removed from the barrel 96, the user may press the applicator 94 against a surgical site on the patient's skin surface to apply the antiseptic composition thereto. When using the skin preparation device 90, the user grips the outer surfaces of the cap 92, thereby reducing the risk of contact with the applicator 94, which could potentially contaminate the antiseptic composition. Further, when removing the cap 92 from the barrel 96, the user need only grip the cap 92 and the barrel 96.

In one non-limiting embodiment or aspect, the cap 92 is made of a PPA material (Polyphthalamide, which is good for maintaining sterility) and may have serrations on the outer surface thereof. The serrations are provided so that a user can hold the cap 92 easily and then the applicator 94 and the cap 92 as a unit may move on the patient's skin surface where site preparation is required. In one non-limiting embodiment or aspect, the barrel 96 may be made of PPA or Polyvinylidene fluoride (PVDF).

The skin preparation devices 2, 20, 30, 50, 80, 90 of the present disclosure enable aseptic non-touch skin preparation for intravenous (IV) line insertion, especially for peripheral intravenous catheters (PIVC). Furthermore, the skin preparation devices 2, 20, 30, 50, 80, 90 and the packaging 40, 64, 86 result in low cost device and adequately treat patients in a price-conscious market. The skin preparation devices 2, 20, 30, 50, 80, 90 provide improved gripping arrangements for the disinfectant wipes to avoid accidental touching of the active surface of the wipe intended for skin preparation. In addition, the packaging 40, 64, 86 is also be optimized to aid in the aseptic non-touch technique. The present disclosure adds minimal cost to the current low cost wipes in terms of providing handles for aseptic non-touch holding of the wipes and adjusting rigidity of the wipe for easy grabbing of the handle.

The current disclosure utilizes the device design (creatively making the gripping portion of the same material as the wipe for aseptic use of the skin preparation), material science (optimized rigidity of the wipes for the gripping portion for easy access and optimized porosity of the wipe to retain the required amount of disinfectant liquid and at the same time not dripping when taken out from the packaging), and packaging features (packaging direction for opening the packaging with the gripping portion directed towards the user and tear pattern perpendicular to the gripping portion for the gripping portion to spring outwardly when the package is teared to enable easy gripping portion access).

The device material property is one important factor in this disclosure. Optimized rigidity of the wipe material enables the gripping portion to spring out when the packaging is opened and at the same time remain inside the packaging without damaging it over the shelf life. Optimized porosity of the packaging material results in the required amount of disinfectant liquid incorporated into the device and at the same time not dripping when the device is taken out of the packaging over the product shelf life.

The present disclosure provides an improved combination of device design, material properties, and packaging features to address the shortcomings of wipes in skin preparation, i.e. being able to aseptic non-touch application of skin preparation device. A gripping portion made of the same material as the wipe provides cost effective means to incorporate this feature for a price sensitive market.

While the present invention has been described in terms of the above detailed description, those of ordinary skill in the art will understand that alterations may be made within the spirit of the invention.

What is claimed is:

1. A skin preparation device for applying an antiseptic composition to skin of a patient, comprising:

an applicator configured to absorb the antiseptic composition, the applicator comprising a top surface and a bottom surface, the bottom surface configured to apply the antiseptic composition to the skin of the patient; and a holding portion that receives the applicator to provide a portion of the skin preparation device that is gripped by a user when using the skin preparation device, wherein the holding portion defines a cavity that receives at least a portion of the applicator, and wherein the cavity comprises a round cross-sectional shape that corresponds to a round cross-sectional shape of a portion of the applicator.

2. The skin preparation device of claim 1, wherein the applicator and the holding portion are made of a different material.

3. The skin preparation device of claim 1, wherein the applicator is made of a sponge material and the holding portion is made of a plastic material.

4. The skin preparation device of claimed in claim 1, wherein the holding portion includes at least one reinforcing member to provide support to the applicator.

5. The skin preparation device of claim 1, wherein the applicator is at least one of a natural sponge and a synthetic sponge.

6. The skin preparation device of claim 5, wherein the synthetic sponge comprises at least one of a polyurethane, a polyester, and/or a vegetal cellulose.

7. The skin preparation device of claim 1, wherein the antiseptic composition includes one or more alcohols, comprising ethyl alcohol, propyl alcohol, isopropyl alcohol, n-propanol, and/or mixtures thereof.

8. The skin preparation device of claim 1, wherein the antiseptic composition includes one or more non-alcohol based compounds.

9. The skin preparation device of claim 8, wherein the one or more non-alcohol based compounds comprise at least one of iodine, para-chloro-meta-xylenol, bis-biguanides, chlorhexidine gluconate (CHG), chlorhexidine diacetate, a quaterium class compound, benzethonium chloride, benzalkonium chloride, chloroxylenol, triclosan, hexachlorophene, octenidine, diazolidinyl urea, methyl chloro isothiazoline, methyl isothiazoline, triclosan, and/or mixtures thereof.

10. The skin preparation device of claim 1, wherein the antiseptic composition includes a mixture of alcohol and non-alcohol based compounds.

11. The skin preparation device of claim 1, wherein the antiseptic composition includes CHG and an alcohol.

12. The skin preparation device of claim 11, wherein the alcohol is isopropyl alcohol.

13. The skin preparation device of claim 12, wherein the antiseptic composition includes about 2% (w/v) CHG and about 70% (v/v) isopropyl alcohol.

* * * * *